United States Patent
Tomioka

(10) Patent No.: US 8,072,483 B2
(45) Date of Patent: Dec. 6, 2011

(54) ENDOSCOPE OPTICAL SYSTEM AND ENDOSCOPE

(75) Inventor: Makoto Tomioka, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 12/932,202

(22) Filed: Feb. 18, 2011

(65) Prior Publication Data

US 2011/0199471 A1 Aug. 18, 2011

Related U.S. Application Data

(63) Continuation of application No. PCT/JP2010/061942, filed on Jul. 15, 2010.

(30) Foreign Application Priority Data

Jul. 30, 2009 (JP) ................................. 2009-177784

(51) Int. Cl.
| H04N 13/00 | (2006.01) |
| A61B 1/04 | (2006.01) |
| G02B 23/00 | (2006.01) |
| G02B 23/24 | (2006.01) |

(52) U.S. Cl. ............. 348/45; 348/65; 359/431; 359/434
(58) Field of Classification Search .................... 348/45, 348/65; 359/431, 434
See application file for complete search history.

(56) References Cited

U.S. PATENT DOCUMENTS

| 4,720,178 A * | 1/1988 | Nishioka et al. .............. 359/431 |
| 4,746,203 A | 5/1988 | Nishioka et al. |
| 6,560,013 B1 * | 5/2003 | Ramsbottom ................. 359/431 |
| 6,638,216 B1 | 10/2003 | Durell |
| 2002/0026098 A1 * | 2/2002 | Kobayashi .................... 600/160 |
| 2006/0252995 A1 | 11/2006 | Hoeg et al. |
| 2006/0256450 A1 | 11/2006 | Tesar et al. |

FOREIGN PATENT DOCUMENTS

| JP | 58-105211 | 6/1983 |
| JP | 62-096923 | 5/1987 |
| JP | 2006-201796 | 8/2006 |
| JP | 2006-204924 | 8/2006 |

OTHER PUBLICATIONS

International Search Report, issued in corresponding International Application No. PCT/JP2010/061942.

* cited by examiner

*Primary Examiner* — David Czekaj
*Assistant Examiner* — Anner Holder
(74) *Attorney, Agent, or Firm* — Kenyon & Kenyon LLP

(57) ABSTRACT

Provided is an endoscope optical system including first deflecting means that deflects light incident along an incident optical axis in a direction along a first axis perpendicular to the incident optical axis and emits the light; second deflecting means having two reflecting faces that fold back the light emitted from the first deflecting means along a second axis separated from the first axis by a gap; and third deflecting means that deflects the light folded back by the second deflecting means in a direction perpendicular to the first axis and along a plane including the incident optical axis, wherein the first deflecting means is provided so as to be capable of swiveling about the first axis relative to the second deflecting means, and the two reflecting faces of the second deflecting means are disposed to form an obtuse angle therebetween.

26 Claims, 5 Drawing Sheets

ENDOSCOPE OPTICAL SYSTEM AND ENDOSCOPE

CROSS-REFERENCE TO RELATED APPLICATIONS

This is a continuation of International Application PCT/JP2010/061942, with an international filing date of Jul. 15, 2010, which is hereby incorporated by reference herein in its entirety.

BACKGROUND OF THE INVENTION

1. Field of the Invention

The present invention relates to endoscope optical systems and endoscopes.

2. Description of Related Art

In known endoscopes in the related art, the viewing direction of the endoscope can be changed by swiveling or rotating a prism disposed in a tip portion of the endoscope to change the orientation of the distal end face thereof (for example, see U.S. Pat. No. 6,638,216 and Japanese Unexamined Patent Application, Publication No. 2006-201796).

In the endoscope disclosed in U.S. Pat. No. 6,638,216, the prism is disposed at a position shifted in the diameter direction from the optical axis of other optical systems inside the endoscope and moves in the diameter direction inside the endoscope.

In the endoscope disclosed in Japanese Unexamined Patent Application, Publication No. 2006-201796, the prism is disposed so as to protrude in the diameter direction from the tip portion of the endoscope, and the optical axis of an optical system from the prism to an image sensor is orthogonal to the optical axis of the main endoscope body.

BRIEF SUMMARY OF THE INVENTION

A first aspect of the present invention is an endoscope optical system including a first prism that deflects light incident along an incident optical axis in a direction along a first axis perpendicular to the incident optical axis and emits the light; a second prism having two reflecting faces that fold back the light emitted from the first prism along a second axis separated from the first axis by a gap; and a third prism that deflects the light folded back by the second prism in a direction perpendicular to the first axis and along a plane including the incident optical axis, wherein the first prism is provided so as to be capable of swiveling about the first axis relative to the second prism, and the two reflecting faces of the second prism are disposed to form an obtuse angle therebetween.

A second aspect of the present invention is an endoscope optical system including a first prism that deflects light incident along an incident optical axis in a direction along a first axis that intersects the incident optical axis and emits the light; a second prism having two reflecting faces that fold back the light emitted from the first prism along a second axis separated from the first axis by a gap and perpendicular to the incident optical axis; and a third prism that deflects the light folded back by the second prism in a direction perpendicular to the second axis and along a plane including the incident optical axis, wherein the first prism and the second prism are provided so as to be capable of swiveling about the second axis relative to the third prism, and the two reflecting faces of the second prism are disposed to form an obtuse angle therebetween.

A third aspect of the present inventions is an endoscope including an endoscope optical system according to the above-described first aspect or second aspect at a tip of an inserted portion.

DETAILED DESCRIPTION OF THE INVENTION

An endoscope optical system 1 and an endoscope 100 equipped with this endoscope optical system 1 according to a first embodiment of the present invention will be described below with reference to FIGS. 1 to 5.

Figure 1:
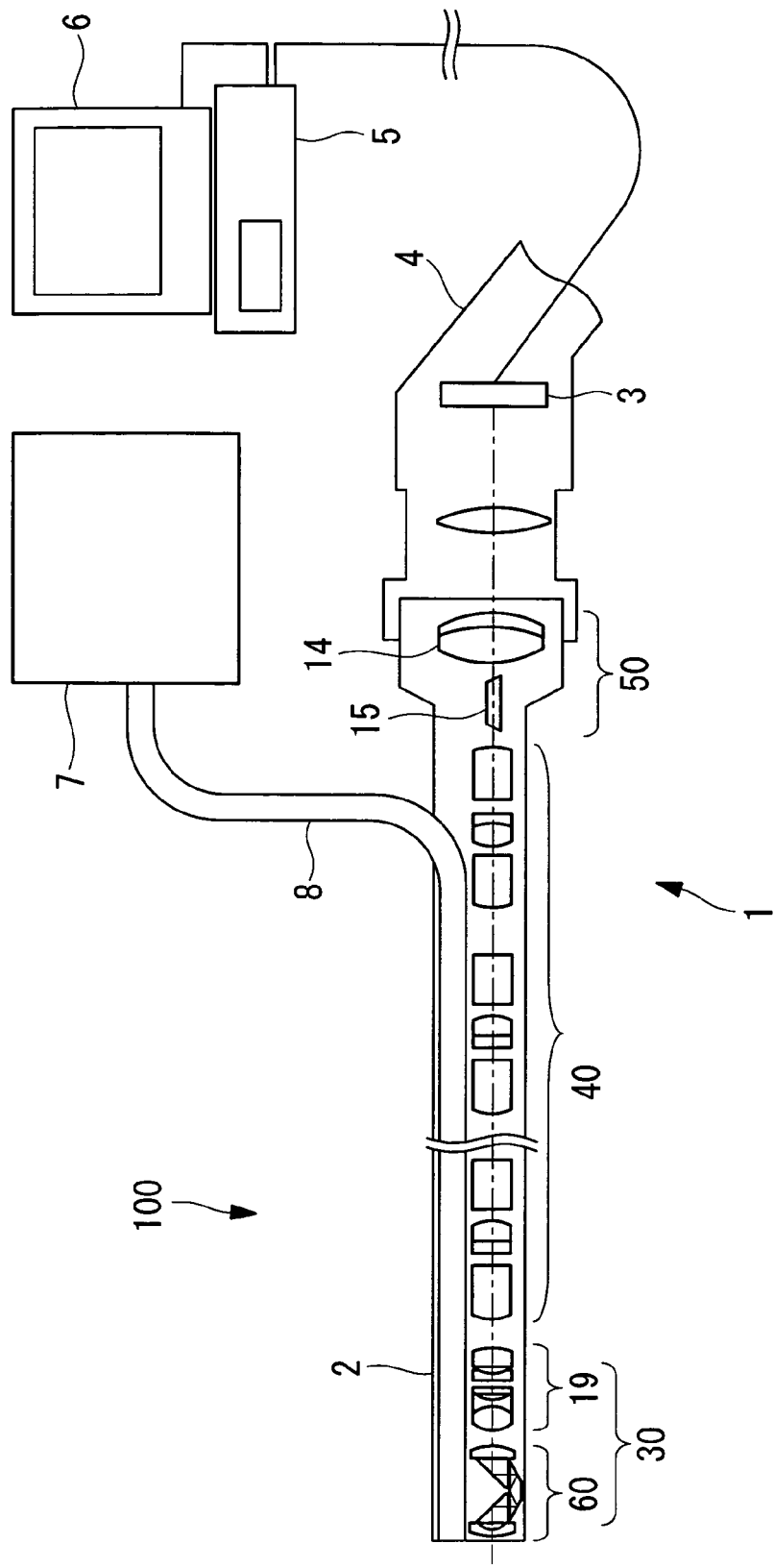
FIG. 1 is a diagram of the overall configuration of an endoscope optical system and endoscope according to a first embodiment of the present invention.

As shown in FIG. 1, the endoscope 100 according to this embodiment is a rigid endoscope having a straight tube-shaped rigid lens barrel 2 in an inserted portion. The endoscope optical system 1 according to this embodiment is disposed inside the lens barrel 2.

A camera head 4 including an image-acquisition device (image-acquisition unit) 3 is mounted at the base end of the endoscope 100. Image information acquired by the image-acquisition device 3 is transferred to a processor 5 as a digital signal. The processor 5 generates an image from the input digital signal and displays it on a monitor 6. A light guide 8 that is connected to a light source 7 is disposed along the longitudinal direction inside the lens barrel 2. Light from the light source 7 is guided by the light guide 8 and is thereby radiated in the forward direction from the distal end face of the endoscope 100.

The endoscope optical system 1 includes, in order from the distal end face of the lens barrel 2, an objective optical system 30 that images light coming from an object, a relay optical system 40 that relays the image formed by the objective optical system 30, and an eyepiece optical system 50 for observing the image relayed by the relay optical system 40.

Figure 2:
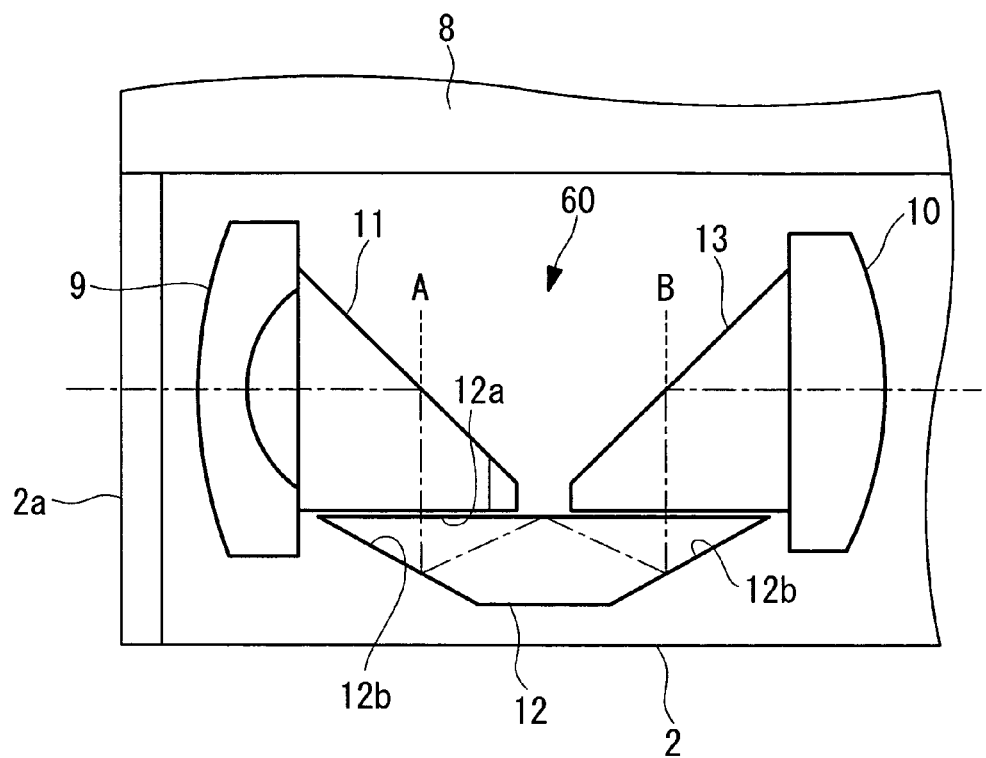
FIG. 2 is a diagram showing a first unit of an objective optical system in the endoscope in FIG. 1.

The objective optical system 30 includes a first unit 60 and a lens group 19. As shown in FIG. 2, the first unit 60 includes a concave lens 9, a first prism (first deflecting means) 11, a second prism (second deflecting means) 12, a third prism (third deflecting means) 13, and a plano-convex lens 10. The plano-convex lens 10 emits a substantially collimated beam. The lens group 19 images the substantially collimated beam coming from the plano-convex lens 10. Reference symbol 2a indicates a glass cover covering the distal end face of the lens barrel 2.

The optical axes of the concave lens 9 and the plano-convex lens 10 are disposed coaxially along the longitudinal direction of the lens barrel 2.

In the first and third prisms 11 and 13, right-angled prisms whose cross-sections are right-angled isosceles triangles form the basic shapes. The first and third prisms 11 and 13 are disposed so that the inclined faces thereof oppose each other to form a right angle, and one of the faces on either side of the 90° interior angles is orthogonal to the optical axes of the concave lens 9 and the plano-convex lens 10 at substantially the center thereof. Also, the first and third prisms 11 and 13 have shapes formed by cutting off the tips of the 45° angles that neighbor each other.

The second prism 12 is trapezoidal prism-shaped in cross-section. The second prism 12 is disposed so that a bottom face 12a thereof is parallel to the other one of the faces on either side of the 90° interior angles of the first prism 11 and the third prism 13, with a minute gap therebetween. Regarding the second prism 12, the size of the base angles formed by the bottom face 12a and inclined faces 12b is designed such that light perpendicularly incident on the bottom face 12a from the first prism 11 is reflected three times between the inclined faces (reflecting faces) 12b and the bottom face 12a and is perpendicularly emitted towards substantially the center of the other of the faces on either side of the 90° interior angle of the third prism 13.

As shown by the one-dot chain line in FIG. 2, the light emitted from the concave lens 9 is deflected by a right angle at the inclined face of the first prism 11, and is thereby incident on the second prism 12 along a first axis A orthogonal to the bottom face 12a. Then, the light entering the second prism 12 is reflected three times between the inclined faces 12b and the bottom face 12a and then enters the third prism 13 along a second axis B orthogonal to the bottom face 12a. The light entering the third prism 13 is deflected rearward along the longitudinal direction of the lens barrel 2 and is then formed into a substantially collimated beam by the plano-convex lens 10 and is emitted therefrom.

Figure 3:
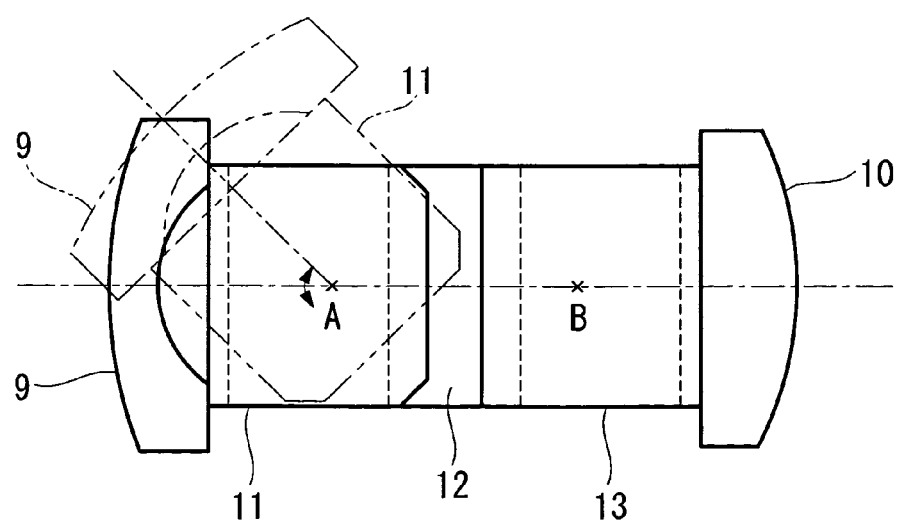
FIG. 3 is a diagram for explaining the operation of the first prism.

As shown in FIG. 3, the first prism 11 and the concave lens 9 are joined and are provided in such a manner that they can be swiveled as a single unit about an axis passing through the intersection of the inclined face of the first prism 11 with the optical axis of the concave lens 9 and orthogonal to the optical axis of the concave lens 9, in other words, the first axis A. The first prism 11 and the concave lens 9 continuously swivel, for example, from −45° to +45°, preferably from −60° to +60°, relative to the front direction of the distal end face of the endoscope 100. Accordingly, the angle of the viewing direction of the endoscope 100 is continuously varied between −45° and +45°, preferably between −60° and +60°, relative to this front direction. More preferably, the angle is continuously varied between −90° and +90°. Note that, so that the first prism 11 swivels without interfering with the third prism 13, the shape of the first prism 11 may be appropriately modified to the extent that it does not have any influence on the light path, such as chamfering the corners of the first prism 11 adjacent to the third prism 13.

The relay optical system 40 images, an even number of times, the light imaged by the objective optical system 30 at intermediate positions thereof, thereby forming a mirror image at the final image plane.

The eyepiece optical system 50 includes an eyepiece lens 14 that magnifies the image formed at the final image plane of the relay optical system 40 and emits light in the form of a collimated beam.

The eyepiece optical system 50 includes an image-rotating prism 15 disposed between the relay optical system 40 and the eyepiece lens 14. The image-rotating prism 15 is trapezoidal prism-shaped in cross-section. The image-rotating prism 15 reflects, at the bottom face thereof, the light incident from one inclined face along a prescribed optical axis parallel to the bottom face and emits the light along the same prescribed optical axis as the incident light from the other inclined face. During this process, the image that the emitted light forms is a mirror image of the image that the incident light forms.

The image-rotating prism (rotation correcting mechanism) 15 has a prescribed optical axis disposed on a line extending from the optical axis of the relay optical system 40 and is provided so as to be rotatable about the prescribed optical axis. During this time, in synchronization with the swiveling of the first prism 11, the image-rotating prism 15 is configured to rotate by an angle equal to half of the angle through which the first prism 11 swivels, in a direction that corrects the rotation of the image at the image-acquisition device 3 due to the first prism 11 swiveling. Accordingly, even though the first prism 11 is made to swivel, the orientation of the image formed on the image-acquisition device 3 is kept fixed.

The operation of the rigid endoscope 100 equipped with the thus-configured endoscope optical system 1 will be described below.

To observe the interior of a body using the rigid endoscope 100 equipped with the endoscope optical system 1 according to this embodiment, the endoscope 100 is inserted inside the body from the distal end while illuminating the forward direction with the light guide 8, which makes it possible to observe an endoscope image of the body interior on the monitor 6. By swiveling the first prism 11 at this time, it is possible to observe the body interior while changing the viewing direction to a direction tilted from the front direction.

According to this embodiment, even with the rigid endoscope 100, whose distal end face cannot be changed in orientation because of its structure, due to the simple configuration using the three prisms 11, 12, and 13, an advantage is afforded in that it is possible to observe a wide area while continuously changing the viewing direction.

The first and third prisms 11 and 13 are disposed on the optical axis of the other optical systems 40 and 50 disposed behind them. Furthermore, by employing a configuration that reflects the light from the first prism 11 to the third prism 13 three times by using a trapezoidal component in the second prism 12, whose inclined faces 12b form an obtuse angle therebetween, the second prism 12 can be reduced to a comparatively small size in the diameter direction of the lens barrel 2. Accordingly, an advantage is afforded in that it is possible to reduce the outer diameter of the tip portion of the endoscope 100.

By reducing the size of the endoscope optical system 1 in the diameter direction of the endoscope 100, for the lenses constituting the objective optical system 30 and the relay optical system 40, it is possible to use lenses with diameters that make adequate use of the space inside the lens barrel 2. Accordingly, an advantage is afforded in that it is possible to obtain an endoscope image with excellent image quality that rivals conventional rigid endoscopes whose viewing direction is fixed, by using lenses with excellent performance in terms of numerical aperture, aberration correction, and so forth, for each lens.

Furthermore, by using the image-rotating prism 15, an advantage is afforded in that it is possible to correct, with high precision and a simple configuration, the image rotation occurring when the first prism 11 is swiveled.

In the embodiment described above, the first prism 11 and the concave lens 9 are provided in such a manner that they can be swiveled as a single unit; instead of this, however, the first prism 11, the second prism 12, and the concave lens 9 may be provided in such a manner that they can be swiveled as a single unit.

In this case, the first prism 11, the second prism 12, and the concave lens 9 are swiveled about the second axis B. By doing so, it is also possible to reduce the diameter of the endoscope 100 while still making the viewing direction variable.

In the above-described embodiment, the first prism 11 is continuously swivelable; instead of this, however, it may be configured to be swivelable in steps at prescribed angles.

For example, even when the first prism 11 swivels in steps at 0°, ±30°, ±45°, and ±90° relative to the front direction of the distal end face of the endoscope 100, it is possible to observe a suitably wide field of view.

In the above-described embodiment, a prism with a trapezoidal prism-shaped cross-section is used as the image-rotating prism 15; however, the image-rotating prism 15 may have a shape whose incident light and exit light axes are the same and which internally reflects the light an odd number of times.

Figure 4:
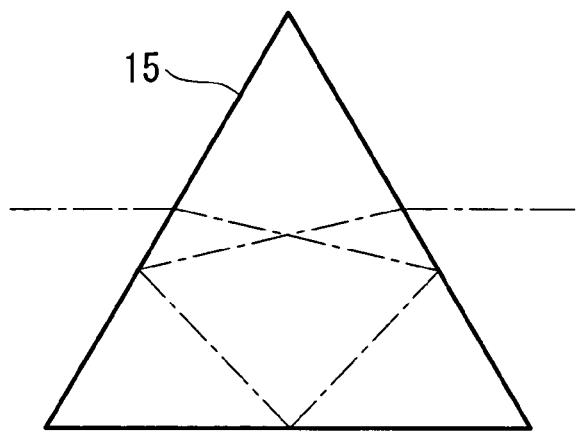
FIG. 4 is a diagram showing a modification of an image-rotating prism.
Figure 5:
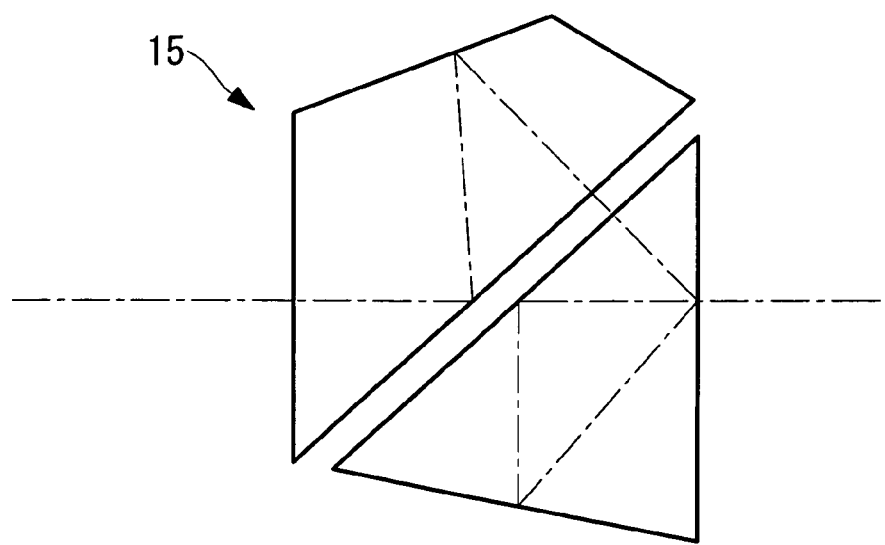
FIG. 5 is a diagram showing another modification of the image-rotating prism.

For example, as shown in FIG. 4, it may be a prismatic prism whose cross-section is an equilateral triangle, or as shown in FIG. 5, it may be a combination of a plurality of prism with different shapes. These prisms can also correct the image rotation by being rotated about the optical axis of the incident light and the exit light.

In the above-described embodiment, the second prism 12 reflects the light that is incident from the first prism 11 three times; however, the number of reflections may be an odd number greater than or equal to three.

By increasing the distance between the first prism 11 and the third prism 13 along the longitudinal direction of the lens barrel 2, it is possible to increase the number of reflections inside the second prism 12, and as a result, it is possible to further reduce the size of the second prism 12 in the diameter direction of the lens barrel 2.

In the above-described embodiment, the image rotation is corrected by the image-rotating prism 15; however, it may be electrically corrected by a processor.

Next, an endoscope optical system 1 and an endoscope 100 provided with this endoscope optical system 1 according to a second embodiment of the present invention will be described below with reference to FIG. 6 and FIG. 7.

Structures in common with those of the first embodiment are assigned the same reference numerals and a description thereof will be omitted.

Figure 6:
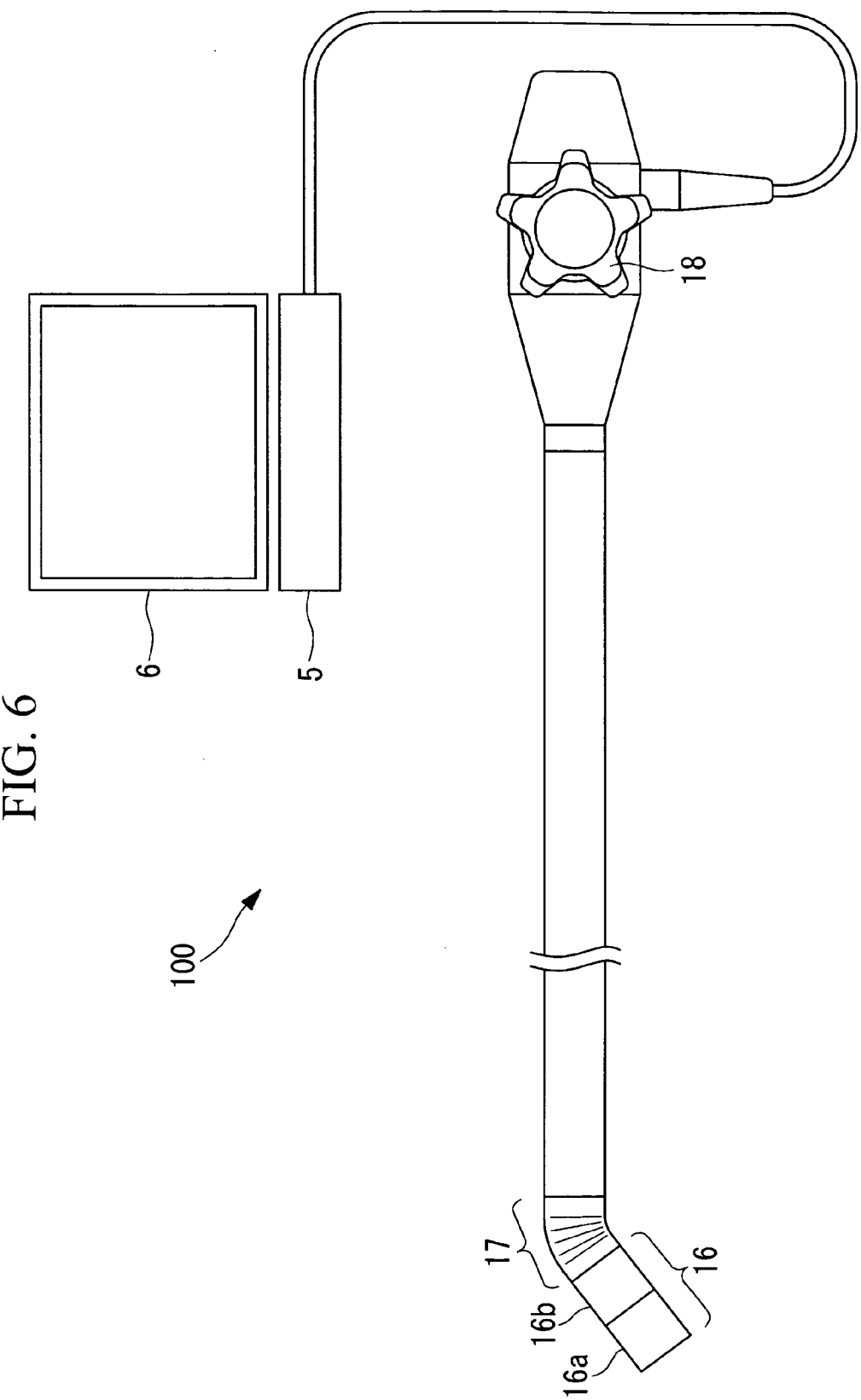
FIG. 6 is a diagram of the overall configuration of an endoscope according to a second embodiment of the present invention.

As shown in FIG. 6, the endoscope 100 according to this embodiment uses a laparoscope having a tip portion 16 in which is disposed an optical system for collecting light from an object and for forming and capturing an image thereof and a bending portion 17 that changes the orientation of the tip portion 16. The endoscope optical system 1 according to this embodiment is disposed inside the tip portion 16.

The endoscope 100 transfers image information acquired at the tip portion 16 to an external processor 5 as a digital signal.

A lens barrel of the tip portion 16 includes a front tube 16a and a rear tube 16b, in this order from the distal end. The front tube 16a and the rear tube 16b are provided in such a manner that they can rotate in the circumferential direction independently of each other, relative to the bending portion 17. The bending portion 17 is made to bend by an operator manipulating a knob 18.

Figure 7:
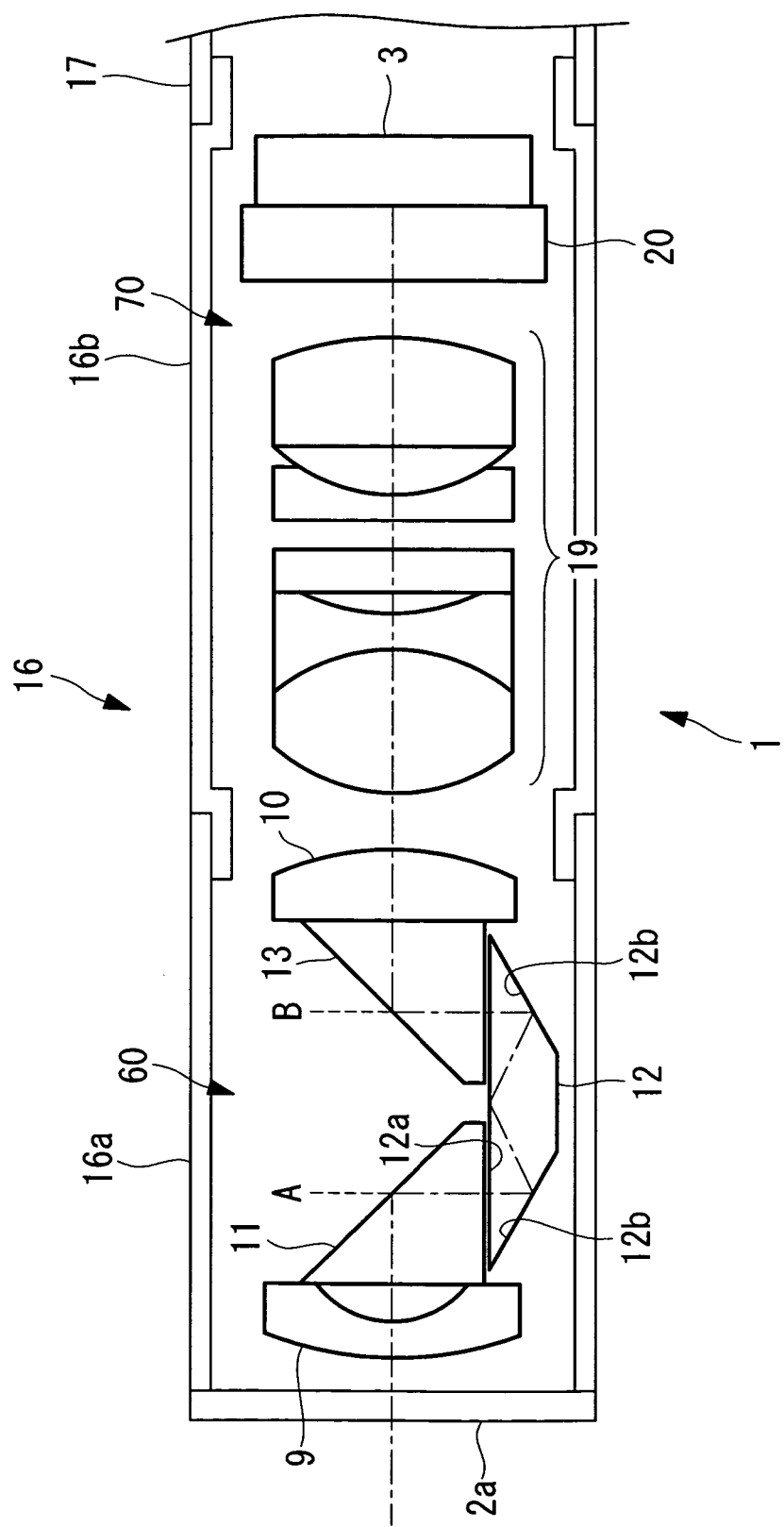
FIG. 7 is an diagram showing the overall configuration of an endoscope optical system according to the second embodiment of the present invention, showing an expanded view of a tip portion of the endoscope in FIG. 6.

As shown in FIG. 7, the endoscope optical system 1 according to this embodiment includes a first unit 60 disposed inside the front tube 16a and a second unit 70 provided with an image-acquisition device 3 disposed inside the rear tube 16b.

The first unit 60 has the same configuration as in the first embodiment. The optical axes of the concave lens 9 and the plano-convex lens 10 are disposed so as to be aligned with the center axis of the front tube 16a. The first unit 60 is integral with the front tube 16a and rotates about the center axis of the front tube 16a by rotating the front tube 16a in the circumferential direction. By doing so, the direction in which it is possible to swivel the first prism 11 relative to the main body of the endoscope 100 is changed. In other words, the variable viewing direction, for example, the left/right direction or the up/down direction relative to the field of view, is optionally set to any direction.

The second unit 70 includes a lens group 19 for conveying the substantially collimated beam emitted from the first unit 60 to the image-acquisition device 3. Reference numeral 20 indicates a sealing glass member for protecting the image-acquisition surface of the image-acquisition device 3. The second unit 70 is integral with the rear tube (rotation correcting mechanism) 16b. When the rear tube 16b is rotated in the circumferential direction, the second unit 70 is also provided in such a manner that it can rotate about the center axis of the rear tube 16b. At this time, in synchronization with the swiveling of the first prism 11, the rear tube 16b is rotated by the same angle as the first prism 11 in a direction which corrects the image rotation relative to the image-acquisition device 3 by swiveling the first prism 11.

The operation of the thus-configured endoscope 100 provided with the endoscope optical system 1 will be described below.

To observe the interior of an abdominal cavity using the endoscope 100 according to this embodiment, by inserting the tip portion 16 into the abdominal cavity from a small hole formed in advance in the abdominal cavity while illuminating the frontward direction with a light guide or the like, which is not shown, an endoscopic image of the interior of the abdominal cavity is displayed on a monitor 6. Then, by swiveling the first prism 11, it is possible to observe a field of view in an inclined direction relative to the front direction of the distal end face. By rotating the front tube 16a in the circumferential direction, with the field of view kept stationary on the monitor 6, the variable viewing direction is changed, and it is possible to point the viewing direction in a desired direction, such as the left/right direction or the up/down direction.

Thus, according to this embodiment, the viewing direction is changed even though the bending portion 17 is not bent. Accordingly, it is possible to observe a wide area, even at narrow locations the cavity where it is difficult to change the orientation of the tip portion 16. Also, when using another surgical instrument at the same time as observation with the endoscope 100, an advantage is afforded in that it is possible to prevent the tip portion 16 from hindering the manipulation of the surgical instrument, making it possible to ensure a wide space for manipulating the surgical instrument. In addition, by swiveling the first prism 11 when the bending portion 17 is in a bent state, an advantage is afforded in that it is possible to perform observation in a desired direction even at intricate sites where observation is conventionally difficult.

Between the first unit 60 and the second unit 70, the beam is substantially afocal. Therefore, an advantage is afforded in that, when the second unit 70 is rotated, even if the position of the second unit 70 is shifted somewhat relative to the first unit 60, it is possible to obtain a stable image by suppressing focal point blurring, image wobbling, and the like.

When the first tube 16a is rotated to change the variable viewing direction, the orientation of the image-acquisition device 3 relative to the field of view is kept fixed; therefore, unlike the case where the entire endoscope 100 is rotated in the circumferential direction, the endoscope image output on the monitor 6 remains fixed in the up/down and left/right directions. Accordingly, when the operator manipulates the endoscope 100, another surgical instrument, etc. while viewing the endoscope image, even though the viewing direction is changed to various directions, an advantage is afforded in that it can be correctly manipulated without confusing one's sense of direction relative to the field of view.

In the above-described embodiment, the image-acquisition device 3 and the lens group 19 are rotated in synchronization with the swiveling of the first prism 11; instead of this, however, the image-acquisition device 3 alone may be rotated.

In this case too, it is possible to correct the image rotation due to the swiveling of the first prism 11.

In the above-described embodiment, a laparoscope having the tip portion 16 and the bending portion 17 is used as the endoscope 100; however, a flexible endoscope may be used instead.

A hard tip portion of the flexible endoscope includes and an objective optical system that collects light coming from the object and an image-acquisition device and has an optical system configuration similar to the tip portion 16 of the endoscope 100 according to this embodiment. Many flexible endoscopes include a channel for passing a surgical instrument in addition to an optical system for image acquisition, and the space in which the optical system can be disposed is limited relative to the diameter thereof. Therefore, the endoscope optical system 1 according to this embodiment can also be suitably used in flexible endoscopes.

What is claimed is:

1. An endoscope optical system comprising:
   a first prism that deflects light incident along an incident optical axis in a direction along a first axis perpendicular to the incident optical axis and emits the light;
   a second prism having two reflecting faces that fold back the light emitted from the first prism along a second axis separated from the first axis by a gap; and
   a third prism that deflects the light folded back by the second prism in a direction perpendicular to the first axis and along a plane including the incident optical axis,
   wherein the first prism is provided so as to be capable of swiveling about the first axis relative to the second prism, and
   the two reflecting faces of the second prism are disposed to form an obtuse angle therebetween.

2. An endoscope optical system according to claim 1, wherein:
   the first and third prisms reflect the incident light one time; and
   the second prism reflects the light an odd number of times greater than or equal to 3.

3. An endoscope optical system according to claim 1, comprising an image-acquisition unit, on an exit optical axis from the third prism, that acquires an image formed by imaging the light emitted from the third prism,
   and comprising a rotation correcting mechanism that rotates the image about the exit optical axis relatively with respect to the image-acquisition device, in synchronization with the swiveling of the first prism, in a direction that corrects the rotation of the image relative to the image-acquisition unit when the first prism is swiveled.

4. An endoscope optical system according to claim 3, wherein the rotation correcting mechanism rotates the image-acquisition unit about the exit optical axis by a swivel angle identical to that of the first prism.

5. An endoscope optical system according to claim 3, further comprising:
   a lens group that is disposed between the third prism and the image-acquisition unit and that conveys the light emitted from the third prism to the image-acquisition unit,
   wherein the rotation correcting mechanism rotates the image-acquisition unit and the lens group as a single unit about the exit optical axis by a swivel angle identical to that of the first prism.

6. An endoscope optical system according to claim 5, wherein a light beam between the third prism and the lens group is substantially afocal.

7. An endoscope optical system according to claim 3, wherein the rotation correcting mechanism includes an image-rotating prism at which light is incident thereon and emitted therefrom along a prescribed optical axis, the prescribed optical axis being disposed on the exit optical axis between the third prism and the image-acquisition unit, and which is provided so as to be capable of rotating about the prescribed optical axis.

8. An endoscope optical system according to claim 7, wherein the image-rotating prism is rotated by an angle equal to half of the swivel angle of the first prism.

9. An endoscope optical system according to claim 7, wherein the first, second, and third prisms reflect the light an odd number of times as a whole.

10. An endoscope optical system according to claim 1, further comprising:
    a relay optical system that conveys the light emitted from the third prism; and
    an eyepiece optical system for observing an image formed by imaging the light conveyed by the relay optical system,
    wherein the relay optical system images the light an even number of times at intermediate positions.

11. An endoscope optical system according to claim 1, further comprising:
    an image-acquisition unit, on an exit optical axis of the third prism, that acquires an image formed by imaging the light emitted from the third prism,
    wherein the first, second, and third prisms are provided so as to be capable of rotating about the exit optical axis as a single unit relative to the image-acquisition unit.

12. An endoscope comprising an endoscope optical system according to claim 1 at a tip of an inserted portion.

13. An endoscope optical system comprising:
    a first prism that deflects light incident along an incident optical axis in a direction along a first axis that intersects the incident optical axis and emits the light;
    a second prism having two reflecting faces that fold back the light emitted from the first prism along a second axis separated from the first axis by a gap and perpendicular to the incident optical axis; and
    a third prism that deflects the light folded back by the second prism in a direction perpendicular to the second axis and along a plane including the incident optical axis,
    wherein the first prism and the second prism are provided so as to be capable of swiveling about the second axis relative to the third prism, and
    the two reflecting faces of the second prism are disposed to form an obtuse angle therebetween.

14. An endoscope optical system according to claim 13, wherein the first and third prism reflect the incident light one time; and the second prism reflects the light an odd number of times greater than or equal to 3.

15. An endoscope optical system according to claim 13, comprising an image-acquisition unit, on an exit optical axis from the third prism, that acquires an image formed by imaging the light emitted from the third prism, and comprising a rotation correcting mechanism that rotates the image about the exit optical axis relatively with respect to the image-acquisition device, in synchronization with the swiveling of the first prism, in a direction that corrects the rotation of the image relative to the image-acquisition unit when the first prism is swiveled.

16. An endoscope optical system according to claim 15, wherein the rotation correcting mechanism rotates the image-acquisition unit about the exit optical axis by a swivel angle identical to that of the first prism.

17. An endoscope optical system according to claim 15, further comprising:

a lens group that is disposed between the third prism and the image-acquisition unit and that conveys the light emitted from the third prism to the image-acquisition unit, wherein the rotation correcting mechanism rotates the image-acquisition unit and the lens group as a single unit about the exit optical axis by a swivel angle identical to that of the first prism.

18. An endoscope optical system according to claim 17, wherein a light beam between the third prism and the lens group is substantially afocal.

19. An endoscope optical system according to claim 15, wherein the rotation correcting mechanism includes an image-rotating prism at which light is incident thereon and emitted therefrom along a prescribed optical axis, the prescribed optical axis being disposed on the exit optical axis between the third prism and the image-acquisition unit, and which is provided so as to be capable of rotating about the prescribed optical axis.

20. An endoscope optical system according to claim 19, wherein the image-rotating prism is rotated by an angle equal to half of the swivel angle of the first prism.

21. An endoscope optical system according to claim 19, wherein the first, second, and third prisms reflect the light an odd number of times as a whole.

22. An endoscope optical system according to claim 13, further comprising:

a relay optical system that conveys the light emitted from the third prism; and an eyepiece optical system for observing an image formed by imaging the light conveyed by the relay optical system, wherein the relay optical system images the light an even number of times at intermediate positions.

23. An endoscope optical system according to claim 13, further comprising:

an image-acquisition unit, on the exit optical axis of the third prism, that acquires an image formed by imaging the light emitted from the third prism, wherein the first, second, and third prisms are provided so as to be capable of rotating about the exit optical axis as a single unit relative to the image-acquisition unit.

24. An endoscope comprising an endoscope optical system according to claim 13 at a tip of an inserted portion.

25. An endoscope optical system comprising:

first deflecting means that deflects light incident along an incident optical axis in a direction along a first axis perpendicular to the incident optical axis and emits the light;

second deflecting means having two reflecting faces that fold back the light emitted from the first deflecting means along a second axis separated from the first axis by a gap; and third deflecting means that deflects the light folded back by the second deflecting means in a direction perpendicular to the first axis and along a plane including the incident optical axis, wherein the first deflecting means is provided so as to be capable of swiveling about the first axis relative to the second deflecting means, and the two reflecting faces of the second deflecting means are disposed to form an obtuse angle therebetween.

26. An endoscope optical system comprising:

first deflecting means that deflects light incident along an incident optical axis in a direction along a first axis intersecting the incident optical axis and emits the light;

second deflecting means having two reflecting faces that fold back the light emitted from the first deflecting means along a second axis separated from the first axis by a gap and perpendicular to the incident optical axis; and third deflecting means that deflects the light folded back by the second deflecting means in a direction perpendicular to the second axis and along a plane including the incident optical axis, wherein the first deflecting means and the second deflecting means are provided so as to be capable of swiveling about the second axis relative to the third deflecting means, and the two reflecting faces of the second deflecting means are disposed to form an obtuse angle therebetween.

* * * * *